United States Patent
Chae et al.

(10) Patent No.: US 9,839,594 B2
(45) Date of Patent: Dec. 12, 2017

(54) SKIN-MOISTURISING OR WRINKLE-IMPROVING EXTERNAL COMPOSITION AND COSMETIC COMPOSITION

(71) Applicant: KOREA INSTITUTE OF ORIENTAL MEDICINE, Daejeon (KR)

(72) Inventors: Sung Uk Chae, Daejeon (KR); Mi Young Lee, Deajeon (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 21 days.

(21) Appl. No.: 14/651,876

(22) PCT Filed: Oct. 18, 2013

(86) PCT No.: PCT/KR2013/009357
§ 371 (c)(1),
(2) Date: Jun. 12, 2015

(87) PCT Pub. No.: WO2014/092325
PCT Pub. Date: Jun. 19, 2014

(65) Prior Publication Data
US 2015/0328121 A1  Nov. 19, 2015

(30) Foreign Application Priority Data

Dec. 13, 2012 (KR) ........................ 10-2012-0145799

(51) Int. Cl.
| | | |
|---|---|---|
| *A61K 8/63* | (2006.01) | |
| *A61Q 19/00* | (2006.01) | |
| *A61Q 19/08* | (2006.01) | |
| *A61K 31/7048* | (2006.01) | |
| *A61K 36/8964* | (2006.01) | |
| *A61K 8/60* | (2006.01) | |
| *A61K 8/97* | (2017.01) | |
| *A61K 31/7028* | (2006.01) | |
| *A61K 31/704* | (2006.01) | |

(52) U.S. Cl.
CPC ............. *A61K 8/63* (2013.01); *A61K 8/60* (2013.01); *A61K 8/97* (2013.01); *A61K 31/704* (2013.01); *A61K 31/7028* (2013.01); *A61K 31/7048* (2013.01); *A61K 36/8964* (2013.01); *A61Q 19/00* (2013.01); *A61Q 19/007* (2013.01); *A61Q 19/08* (2013.01)

(58) Field of Classification Search
None
See application file for complete search history.

(56) References Cited

U.S. PATENT DOCUMENTS

2012/0316122 A1* 12/2012 Ma ................... A61K 31/58
514/26

FOREIGN PATENT DOCUMENTS

| CN | WO 2011026259 A1 * | 3/2011 | ............ A61K 31/58 |
|---|---|---|---|
| JP | H08-59476 | 3/1996 | |
| JP | 08-133955 | 5/1996 | |
| JP | 08-208424 | 8/1996 | |
| JP | 08-231370 | 9/1996 | |
| JP | 09-040823 | 2/1997 | |
| JP | 10-032283 | 2/1998 | |
| JP | 2007-153813 | 6/2007 | |
| JP | 2011-055743 | 3/2011 | |
| JP | 2012-140618 | 7/2012 | |
| KR | 10-2007-0069566 | 7/2007 | |
| KR | 1020110102682 | 9/2011 | |

OTHER PUBLICATIONS

Norihisa, JP 8133955 A, May 1996, machine translation.*
Cho et al., "Stability of paeoniflorin used as anti-wrinkle agents in emulsions", *J of the Korean Oil Chemists' Soc.*, 26(2): 191-198, 2009. [English Abstract].
Esposito et al., "Nanosystems for skin hydration: a comparative study", *International Journal of Cosmetic Science*, 29: 39-47, 2007.
Kasting and Barai, "Equilibrium water sorption in human stratum corneum", *Journal of Pharmaceutical Sciences*, 92(8): 1624-1631, 2003.
Kim et al., "Isolation and HPLC analysis of Timosaponin A III from rhizomes of *Anemarrhena asphodeloides* bunge", *Korean J. Medicinal Crop Sci.*, 7(1): 45-50, 1999. [English Abstract].
Ko et al., "36kDa glycoprotein isolated from *Rhus verniciflua* stokes fruit has a protective activity to glucose/glucose oxidase-induced apoptosis in NIH/3T3 cells", *Toxicology in Vitro*, 19: 353-363, 2005.
Lee et al., "Antitumor agent from the rhizome of *Anemarrhena asphodeloides*", *Kor J Pharmacogn.*, 26(1): 47-50, 1995. [English Abstract].
Kawasaki et al., "Saponins of Timo (*Anemarrhenae rhizoma*) I", *Yakugaku Zasshi*, 83(9): 892-896, 1963. [English Abstract].
Sato et al., "Studies on chemical protectors against radiation. XXXIII. Protective mechanisms of various compounds against skin injury induced by radiation", *Yakugaku Zasshi*, 111(1): 51-58, 1991. [English Abstract].

* cited by examiner

*Primary Examiner* — Layla Berry
(74) *Attorney, Agent, or Firm* — Parker Highlander PLLC

(57) ABSTRACT

The present invention relates to a skin-moisturizing or wrinkle-improving external composition or cosmetic composition which contains, as an active ingredient, a compound represented by Formula 1, which can be extracted from *Anemarrhena asphodeloides* Bunge, or a pharmaceutically acceptable salt thereof. The composition prevents skin moisture loss and thus suppresses skin tissue damage induced by UV rays and so has a skin-wrinkle preventing or alleviating effect.

1 Claim, 4 Drawing Sheets

CON　　　UV　　　vehicle　　　TM

CON　　　　　UV　　　　　Vehicle　　　　　TM

SKIN-MOISTURISING OR WRINKLE-IMPROVING EXTERNAL COMPOSITION AND COSMETIC COMPOSITION

The present application is a national phase application under 35 U.S.C. §371 of International Application No. PCT/KR2013/009357, filed Oct. 18, 2013, which claims benefit of priority to Korean Application No. 10-2012-0145799, filed Dec. 13, 2012, the entire contents of each of the applications being hereby incorporated by reference.

TECHNICAL FIELD

The present invention relates to a skin-moisturizing or wrinkle-improving external composition or cosmetic composition containing, as an active ingredient, a compound represented by Formula 1, which can be extracted from *Anemarrhena asphodeloides*, or a pharmaceutically acceptable salt thereof.

BACKGROUND ART

Skin is an outer membrane covering the outer surface of human body. As a primary barrier, it plays an important role in protecting and regulating internal organs and external body organs by performing various physiological functions that protect the body from various environmental factors including external stimuli, bathers, dryness, etc. Histologically, when a vertically dissected skin is observed under a microscope, it reveals three primary layers, an epidermis consisting of epithelial tissues, a dermis consisting of connective tissues, and hypodermis consisting of subcutaneous tissues, and each type of tissues exhibits unique physiological functions and has an interactive relationship.

Among these tissues, the connective tissue mainly consists of elastins and collagen fibers, and collagen plays a key role in maintaining the structure of the dermis layer of the skin. Collagen present in the dermis layer accounts for most of the extracellular matrix. Collagen is known to have a functional diversity capable of maintaining the mechanical firmness of skin, strengthening the cohesion of connective tissues and their resistance, supporting cell adhesion, inducing cell division and differentiation, etc. Glycoproteins, such as collagens, elastins, proteoglycans, fibronentins, and lamins, which constitute the extracellular matrix of the dermis layer are mainly produced in fibroblasts and secreted out of the cell. In addition, all nutrients and metabolic wastes are transported and metabolized through the extracellular space. The glycoproteins are involved in numerous cell-surface reactions, and help the skin maintain its elasticity and prevent generation of wrinkles by retaining a large amount of water in the extracellular matrix (Ko, J. H., Lee, S. J., and Lim, K. T., Toxicol. In Vitro, 19, 353, 2005; Cho, W. G., Kyung K. Y., and Yu, S. M., J. of the Korean Chemists, Soc., 26(2), 191, 2009).

Also, the degree of skin-moisturizing, which is considered as an important factor in various industrial fields such as cosmetics, dermatology, and medicine, and particularly, moisturization of cornified layers is directly associated with skin appearance (flexibility and roughness of skin), and becomes a barometer of one's physical condition. Further, the water content in the cornified layer influences the skin barrier homeostasis, which is related to the condition and permeability of skin, and thus the hygroscopicity of cosmetics or topical medications may vary. Therefore, skin moisturization is currently believed to be a crucial factor (Esposito E, Drechsler M, Mariani P, Sivieri E, Bozzini R, Montesi L, Menegatti E, Cortesi r, Int J Cosmet Sci, 29, p 39-47, 2007; Kasting G B, Barai N D, J Pharm Sci, 92, p 1624-31, 200).

Meanwhile, skin aging appears when both intrinsic aging (natural aging), which occurs naturally as people age, and actinic aging occur together. Both types of skin aging share common features of generation of wrinkles and reduction in the components that constitute the Langerhans cells, which are skin immune cells, and dermal cells. The difference between the two lies in that the actinic aging is characterized by skin thickening and an increase in elastic fibers, whereas the intrinsic aging is characterized by skin thinning. A combination of both types of aging may lead to generation of wrinkles. Specifically, on the one hand, as skin tissues age, the human skin fibroblasts present in the dermis layer of the skin also age, and as a consequence, the ability of producing fibers and substrates by the skin is reduced. Subsequently, the overall amount of substrates is reduced, the skin becomes thinned and skin elasticity is deteriorated, thereby forming wrinkles. Alternatively, the skin aging may accelerate wrinkle generation by attacking collagens and fibers, which are responsible for maintaining elasticity of moist, soft, and flexible skin, induced by free radicals and reactive oxygen species (ROS) produced by exposure to ultraviolet radiation. Meanwhile, many studies have shown that, most skin aging occurs due to the exposure to the sun rather than the age-related natural aging. There is a report that more than 80% of wrinkles are generated by the exposure to the sun.

Farmers and fishermen's skins are the representative examples showing the effects of routine exposure to ultraviolet radiation. Their skins are characterized by roughness and deep wrinkles, and distinctive diamond-shaped wrinkles around the scruff of the neck, which is easily exposed to UV rays. Such changes are called the actinic aging, and are distinguished from the changes caused by natural aging. In addition, such symptoms are prominent in the facial area where it may be always exposed to UV rays.

Further, recently, an increasing amount of UV rays is reaching the surface of the earth due to the environmental pollutions, and more chances of being exposed to UV rays due to increasing leisure and outdoor activities, etc. Accordingly, a care to prevent wrinkle generation has become important.

Skin is influenced by UV rays, etc., especially in summer when people enjoy many outdoor activities. As a consequence, the skin becomes rough, and may have a thicker cornified layer and fine wrinkles in autumn. When the skin in this state is in direct contact with dry autumn air, the skin becomes rougher, and the number of fine wrinkles increases rapidly. Further, when winter comes, the drastically decreasing temperature reduces physical activity levels and blood circulation efficiency, which results in prolonging skin's metabolic cycle. Therefore, the skin becomes even rougher, and fine wrinkle generation is considerably accelerated. Furthermore, in order to protect the skin from cold air, the skin itself thickens the cornified layer which makes the skin rougher. Among different parts of skin, the skin having a direct contact with the outside may produce dead skin cells when the dryness is intensified, and become thicker and stiff to stand against the cold air.

Meanwhile, the skin is renewed about every 28 days, that is, the dead cells are raised up to the cornified layer as the new cells are produced, and this is known as cell turn-over cycle. Skin aging begins in women aged 25. The skin aging occurs when the cell turn-over cycle takes longer for various reasons with skin problems (skin troubles), darkening skin tone, reduced skin moisture retention capacity, and finally fine wrinkles. Specifically, the skin becomes rougher and drier inbetween seasons because cold, dry air takes away a large amount of moisture in skin. Furthermore, the skin becomes even drier when the amount of secretion of sweat and sebaceum is dramatically reduced as the metabolic cycle slows down, which accounts for the increase in the dead skin cells on the skin surface.

Due to various reasons mentioned above, the skin may be characterized by thickness in the cornified layer, rough skin, and a rapid increase in fine wrinkles, especially since the age of 25. At this point of time where there is a rapidly growing interest in skin care, there is a desperate need for cosmetics capable of improving such rough skins and fine wrinkles. Specifically, external skin applications such as cosmetics exhibiting superior effects of improving rough skins and fine wrinkles, and simultaneously, confirming safety so that customers can safely use without hesitation are needed.

Thus, various methods for skin moisturization and skin wrinkle improvement have been suggested. For example, extensive studies on skin aging have been developed focusing on the functions that collagens play in the skin to improve the skin wrinkles, and thus, cosmetics containing collagens have become commercially available. However, the cosmetics mixed containing collagen are used by spreading collagen onto the surface of skin, and collagen, which is a polymer, is hardly absorbed into the percutaneous layer, thus unabling to perform its function. Therefore, the effect of wrinkle improvement is insignificant.

Further, there are a few existing substances which are known as collagen synthesis facilitating agents such as retinoic acid, transforming growth factor (TGF, tumor growth factor: Cardinale G. et al., Adv. Enzymol., 41, p. 425, 1974), animal placenta-derived protein (JP 8-231370), betulinic acid (JP 8-208424), and chlorella extract (JP 9-40823, JP 10-36283, a fibroblast growth facilitator), etc. However, their application to the skin makes limitation to the usage amount because of safety issues relating to irritation and rubefaction, and their effects are insignificant, and thus, it is difficult to expect substantial effects of skin improving functions. Accordingly, there is a need to develop an external skin application having a superior wrinkle improvement effect which is safe when applied onto skin.

Under the above circumstances, the present inventors endeavored to study a material having superior skin moisturizing and wrinkle improving effects which is safe to skin, and completed the present invention upon confirming that, when a compound represented by Formula 1 obtained from *Anemarrhena asphodeloides* Bunge was spread onto skins of animal models, the compound improved skin damage of skin bather suppressing the skin damage, thereby alleviating the depth and length of wrinkles, etc.

DISCLOSURE

Technical Problem

An objective of the present invention is to provide a pharmaceutical composition or a cosmetic composition having superior effects on skin moisturization and wrinkle improvement, which contains, as an active ingredient, a compound represented by Formula 1 extracted from *Anemarrhena asphodeloides* Bunge or a pharmaceutically acceptable salt thereof.

Another objective of the present invention is to provide a use of the compound represented by Formula 1 extracted from *Anemarrhena asphodeloides* Bunge or the pharmaceutically acceptable salt thereof for preparing the composition for skin moisturization and wrinkle improvement, or a method for skin moisturization and wrinkle improvement including administration of a therapeutic effective dose of the compound represented by Formula 1 extracted from *Anemarrhena asphodeloides* Bunge or the pharmaceutically acceptable salt thereof to a subject in need thereof.

Technical Solution

To achieve the above objectives, the present invention provides a pharmaceutical composition for skin moisturization and wrinkle improvement containing, as an active ingredient, a compound represented by Formula 1 below or a pharmaceutically acceptable salt thereof.

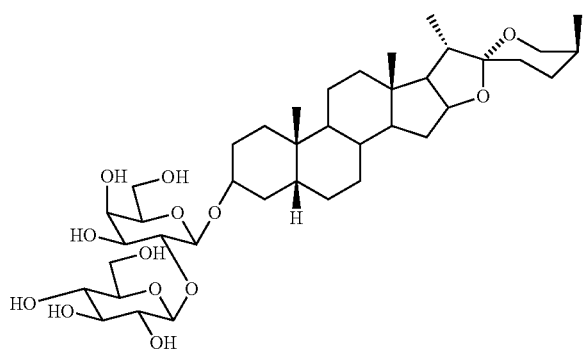

Formula 1

The pharmaceutical composition is preferably for external skin application, but is not limited thereto.

The compound represented by Formula 1 is preferably extracted from *Anemarrhena asphodeloides*. The extraction may be performed using a conventional method known in the art. In one Example of the present invention, the compound represented by Formula 1 was obtained from *Anemarrhena asphodeloides* Bunge using the method described below.

*Anemarrhena asphodeloides* Bunge was subjected to a 3-hour reflux cooling extraction 3 times with ethanol and then concentrated under reduced pressure to obtain an ethanol concentrate. The thus-obtained *Anemarrhena asphodeloides* ethanol concentrate was fractionated into n-hexane, ethyl acetate, and n-butanol in sequence to obtain a n-butanol fraction, and the obtained n-butanol fraction was separated by gradient elution column chromatography using a mixed solution containing water and methanol to obtain five different small fractions. In particular, the ratio of water to methanol used was 10:0 (v/v) to 7:3 (v/v). Among the five small fractions, the fourth small fraction was separated again by gradient elution reversed phase chromatography using a mixed solvent containing water and methanol to obtain a compound represented by Formula 1. In particular, the ratio of water to methanol used was 10:0 (v/v) to 5:5 (v/v).

Meanwhile, the term "*Anemarrhena asphodeloides* Bunge" used herein, is a perennial plant belonging to the monocotyledon Liliales haemodoraceae family, and is usually used as a medicinal ingredient after drying its rhizomes.

According to one Example of the present invention, the compound represented by Formula 1 extracted from *Anemarrhena asphodeloides* Bunge was spread onto the skins of animal models while irradiating UV rays thereonto. As a result, it alleviated the wrinkles deepened by UV rays and had an inhibitory effect on the collagen tissue destruction reaction by suppressing transepidermal water loss.

The compound represented by Formula 1 of the present invention may be used in the form of a pharmaceutically acceptable salt, and examples of the salt may include an acid-added salt formed by a pharmaceutically acceptable free acid and a metal salt formed by a base. Inorganic acids and organic acids may be used as the free acid, and useful examples of inorganic acids include hydrochloric acid, sulfuric acid, bromic acid, sulfurous acid, phosphoric acid, etc., and useful examples of organic acids may include citric acid, acetic acid, maleic acid, fumaric acid, gluconic acid, and methanesulphonic acid, etc. Alkali metal salts or alkali earth metal salts may be used as the metal salt, and sodium, potassium, or calcium may also be useful.

Further, the present invention may further include any material exhibiting skin moisturizing and wrinkle improving effects, including for example, retinol, retinyl palmitate, adenosine, polyethoxylated retinamide, collagen, TGF or animal placenta-derived proteins in addition to the compound represented by Formula 1 extracted from *Anemarrhena asphodeloides* Bunge or the pharmaceutically acceptable salt thereof, but are not limited thereto.

For the purpose of administration, the composition of the present invention may include a pharmaceutically acceptable carrier, an excipient, and a diluting agent, in addition to the active ingredients described above. Examples of those substances may include lactose, dextrose, sucrose, sorbitol, mannitol, xylitol, erythritol, maltitol, starch, *acacia* gum, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, and mineral oil.

According to a conventional method, the composition of the present invention may be used after formulation into an oral administration type, such as powders, granules, tablets, capsules, suspensions, emulsions, syrups, and aerosols, etc., an external application, a suppository, or a sterile injection solution, respectively. Specifically, the formulation may be prepared using a diluting agent or an excipient, such as commonly-used fillers, weighting agents, bonding agents, wetting agents, disintegrating agents, and surfactants. The solid formulations for oral administration include tablets, pills, powders, granules, and capsules, etc., but are not limited thereto. Such solid formulations may be prepared by mixing the compound represented by Formula 1 or the pharmaceutically acceptable salt thereof with at least one excipient, such as starch, calcium carbonate, sucrose, lactose, gelatin, and the like. Also, in addition to simple excipients, lubricants, such as magnesium stearate, and talc, may also be used. Various excipients, such as wetting agents, sweeteners, flavoring agents, and preservatives, in addition to liquids for oral administration and liquid paraffin, may be added to prepare the formulation. The formulations for parenteral administration include sterile aqueous solutions, non-aqueous solvents, suspensions, emulsions, lyophilization formulations, and granules. Examples of the non-aqueous solvents and suspensions include vegetable oil, such as propylene glycol, polyethylene glycol, and olive oil, and an injectable ester, such as ethyl oleate. Witepsol, macrogol, tween 61, cacao butter, laurinum, and glycerol gelatin may be used as the suppository base.

The appropriate dosage (therapeutic effective dosage) of the composition of the present invention may vary depending on various factors including the condition and weight of a patient (subject), the progress of disease, the form of drug, and time, but may be appropriately determined by those skilled in the art. The daily dosage of the compound represented by Formula 1 or the pharmaceutically acceptable salt thereof is preferably 1 mg/kg to 500 mg/kg, and may be administered once or multiple times daily as needed.

Further, the present invention provides a cosmetic composition for skin moisturization and wrinkle improvement containing the pharmaceutical composition.

The composition of the present invention may include conventionally used ingredients in addition to the active ingredients described above, for example, conventional supplements including antioxidants, stabilizing agents, solubilizing agents, vitamins, colorings, and flavorings, and carrier.

The composition of the present invention may be any formulation that is conventionally prepared in the art. For example, it may be formulated into solution, suspension, paste, gel, cream, lotion, powder, soap, surfactant-containing cleanser, oil, powder foundation, emulsion foundation, wax foundation, and spray, etc., but is not limited thereto. More specifically, it may be formulated into softening cosmetic water (toner), nutritive cosmetic water (milky lotion), nourishing cream, massage cream, essence, eye cream, cleansing cream, cleansing foam, cleansing water, mask, spray, or powder.

When the formulation of the present invention is paste, cream, or gel, the ingredients therein may include animal oil, vegetable oil, wax, paraffin, starch, tragacanth, cellulose derivatives, polyethylene glycol, silicon, bentonite, silica, talc, or zinc oxide, etc.

When the formulation of the present invention is powder or spray, the ingredients therein may include lactose, talc, silica, aluminum hydroxide, calcium silicate, or polyamide powder, and particularly, in the case of spray, it may further include a propellant, such as chlorofluorohydrocarbon, propane/butane or dimethyl ester, as an ingredient for the carrier.

When the formulation of the present invention is a solution or an emulsion, the ingredients therein include solvents, solubilizing agents, or emulsifying agents, for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or sorbitan fatty acid ester.

When the formulation of the present invention is a suspension, the ingredients therein include liquid diluting agents, such as water, ethanol, or propylene glycol, suspending agents, such as ethoxylated isostearyl alcohol, polyoxyethylene sorbitol ester, and polyoxyethylene sorbitan ester, and microcrystalline cellulose, aluminum meta-hydroxide, bentonite, agar, or tragacanth.

When the formulation of the present invention is a cleanser containing surfactants, the ingredients therein include aliphatic alcohol sulfate, aliphatic alcohol ether sulfate, sulfosuccinate monoester, isethionate, imidazolium derivatives, methyl taurate, sarcosinate, fatty acid amides ether sulfate, alkyl amido betaine, aliphatic alcohol, fatty acid glyceride, fatty acid diethanolamide, vegetable oils, lanolin derivatives or ethoxylated glycerol fatty acid esters, etc.

Advantageous Effects

The composition containing the compound represented by Formula 1 extracted from *Anemarrhena asphodeloides* Bunge according to the present invention or the pharmaceutically acceptable salt thereof is effective in moisturizing skin and improving wrinkles, especially, preventing or alleviating wrinkles by preventing the skin moisture loss and suppressing the skin tissue damages induced by UV rays.

Accordingly, the composition may be usefully applied to an external skin application or cosmetics having skin-moisturizing and wrinkle-improving effects.

BEST MODE

Figure 1:
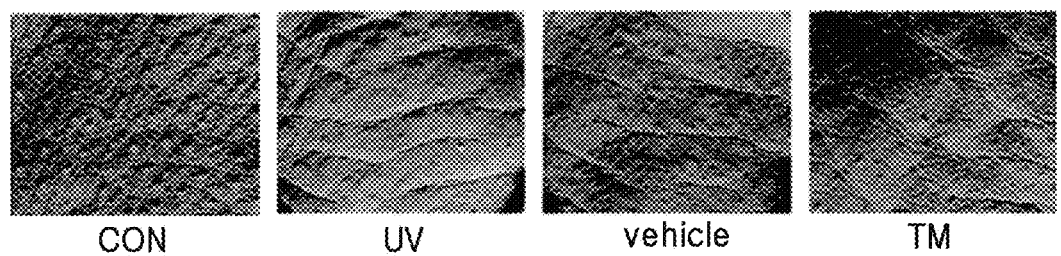
FIG. 1 is an image showing the degree of skin-wrinkle formation of hairless mice using a skin replica according to one embodiment of the present invention.

Hereinafter, the present invention will be described in further detail with reference to examples and preparation examples. It is to be understood, however, that these examples are for illustrative purposes only and are not intended to limit the scope of the present invention.

EXAMPLE

Extraction of the Compound Represented by Formula 1 from *Anemarrhena asphodeloides* Bunge

*Anemarrhena asphodeloides* Bunge was purchased from Omni Hub, and was stored in a refrigerator for herb storage at 5.5±0.3° C. with 55±5% humidity. 3 kg of *Anemarrhena asphodeloides* Bunge was immersed in 70% ethanol of 10 times by volume thereof, and underwent a reflux cooling extraction three times for three hours to prepare the extract. The solvents were removed from the filtrate obtained using a filter paper by a vacuum evaporator to prepare *Anemarrhena asphodeloides* Bunge ethanol extract. The *Anemarrhena asphodeloides* Bunge ethanol extract was sequentially treated with n-hexane, ethyl acetate, and n-butanol to obtain a n-butanol fraction. The thus-obtained n-butanol fraction was separated into 5 small fractions using Diaion hp-20 resin via gradient elution column chromatography using a mixture containing water and methanol. In particular, the ratio of water to methanol used was 10:0 (v/v) to 7:3 (v/v). Among the 5 small fractions, the fourth small-fraction was separated again using RP-18 reverse resin (LiChroprep) via gradient elution column chromatography using a mixture containing water and methanol to obtain a compound represented by Formula 1. In particular, the ratio of water to methanol used was 10:0 (v/v) to 5:5 (v/v).

$^1$H NMR(400 MHz, Pyridine-$d_5$) δ: 0.83 (3H, s, H-18), 0.98 (3H, s, H-19), 1.09 (3H, d, J=6.8 Hz, H-21), 1.17 (3H, d, J=6.4 Hz, H-27), 3.39 (1H, d, J=10.8 Hz, H-26β), 4.94 (1H, d, J =7.6 Hz, H-1'), 5.31 (1H, d, J=7.6 Hz, H-1").

$^{13}$C NMR (100 MHz, Pyridine-$d_5$) δ: 110.0 (C-22), 106.5 (C-1"), 102.9 (C-1'), 82.2 (C-2'), 81.7 (C-16), 78.7 (C-5"), 78.3 (C-3"), 77.3a (C-2"), 76.9 (C-5'), 75.8a (C-3), 75.5a (C-3'), 72.0 (C-4"), 70.2 (C-4), 65 4 (C-26), 63.3 (C-17), 63.1 (C-6"), 62.5 (C-6'), 56.8 (C-14), 42.8 (C-20), 41.2 (C-13), 40.6b (C-12), 40.5b (C-9), 37.3 (C-5), 35.8c (C-10), 35.6c (C-8), 32.5 (C-15), 31.3 (C-1 and C-4), 27.9 (C-25), 27.3 (C-2), 27.1 (C-6 and C-7), 26.7 (C-23), 26.5 (C-24), 24.3 (C-19), 21.5 (C-11), 16.9 (C-18), 16.6 (C-27), 15.2 (C-21).

EXPERIMENTAL EXAMPLE

Analysis of Moisturizing and Wrinkle Improving Effects

Skin-moisturizing and wrinkle-improving effects were confirmed by spreading the compound represented by Formula 1, prepared from the Example, onto the skins of hairless mice.

1) Experimental Animals and Sample Administration 7-week old male hairless mice (male HR-1, hairless mice, Japan SLC, Inc.), the experimental animals, were purchased from Central Lab. Animal Inc (Seoul, Korea). and used after an adaption period of a week. Only healthy animals were used in the experiments by observing general conditions during the adaption period. The breeding environment was maintained at 23±3° C. with 50±5% humidity with a light-dark cycle of 12 hours (7:00-19:00/lighting time). During the experiments, seven experimental animals per each experimental group were raised in a polycarbonate cage (200×320×145 mm, Three-shine Co., Daejeon, Korea), and the animals were given both mouse feed 5L79 (Charles river, USA) and tap water for drinking sterilized with UV rays to be consumed freely.

The experiments were carried out on the following groups: a control group (Con), a UV-treated group (UV), an excipient-treated group (Vehicle), and a group treated by the compound represented by Formula 1 (TM), and the samples were administered thereto. The sample administration was performed for 12 weeks in total by spreading the samples onto skins. For the compound treated group (TM), the compound was dissolved in dimethyl sulfoxide (DMSO), and subsequently in a mixed solution containing propylene glycol, ethanol, and poly ethylene glycol with a 1:1:1 ratio, and the dissolved formulation (the final concentration of the compound was 0.25% (w/v)) was applied to skins with the amount of 40 uL per 6 cm$^2$ once a day for 5 days a week. The excipient-treated group (Vehicle) were treated in the same manner as the compound treated group (TM), except the compound omitted.

Ultraviolet irradiation was performed on the experimental groups except for the control group using a UVB lamp (Mineralight UV Display lamp, UVP, USA) three times a week for 8 weeks. The amount of UV irradiation for the 8 weeks was 60 mJ/cm$^2$ for the first 1 to 2 weeks, 90 mJ/cm$^2$ for the subsequent 3 to 5 weeks, and 120 mJ/cm$^2$ for the subsequent 6 to 8 weeks. The UV irradiance was measured by a radiometry instrument (Delta OHM, Italy), and then, was adjusted according to irradiation time. The UV irradiation variable and the sample amount for each experimental group are shown in Table 1 below.

TABLE 1

|  | UV irradiation | Sample amount |
|---|---|---|
| Control Group (Con) | x |  |
| UV-treated Group (UV) | o |  |
| Excipient-treated Group (Vehicle) | o |  |
| Group treated by compound represented by Formula 1 (TM) | o | 0.25%(w/v) |

2) Skin Wrinkle Measurement

The degree of wrinkle formation was measured with a silicone skin replica of the back skins of the hairless mice of each experimental group. The skin replica was prepared using a Repliflo Cartridge Kit (CuDerm Corporation, USA) by thinly applying the cartridge to the back and completely drying it, followed by peeling off the disk carefully. The preparation of skin replica was carried out under constant temperature and humidity at 20 to 22° C. with 40 to 50% humidity. Then, the skin replica was inserted into a cartridge, which was prepared so that a special light source could pass through, and the light was passed through the replica at an incidence angle of 35°. A shadow image, generated according to the thickness of the skin replica, was filed using a CCD camera, and the depth and length of wrinkles were measured using the Skin Visiometer VL 650 software, which is a computer image analysis system. The results are illustrated in FIGS. 1 to 3.

As shown in FIG. 1, thick, deep wrinkles were induced in the UV-treated group (UV) compared to the control group (CON), whereas thick wrinkles were alleviated in the group treated by compound represented by Formula 1 (TM) compared to the UV-treated group (UV).

Figure 2:
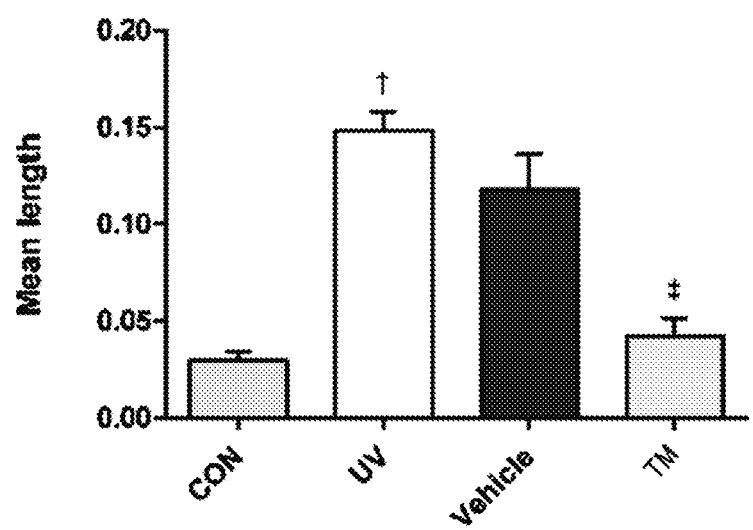
FIG. 2 shows a graph illustrating the changes in the mean length of a skin wrinkle of hairless mice according to one embodiment of the present invention.

As shown in FIG. 2, it was confirmed that the mean wrinkle length was increased in the UV-treated groups (UV) compared to the control group (CON) ($p<0.0001$), whereas the wrinkle mean length was significantly reduced in the group treated by compound represented by Formula 1 (TM) compared to the UV-group (UV) and the excipient-treated group (Vehicle) ($p<0.0001$).

Figure 3:
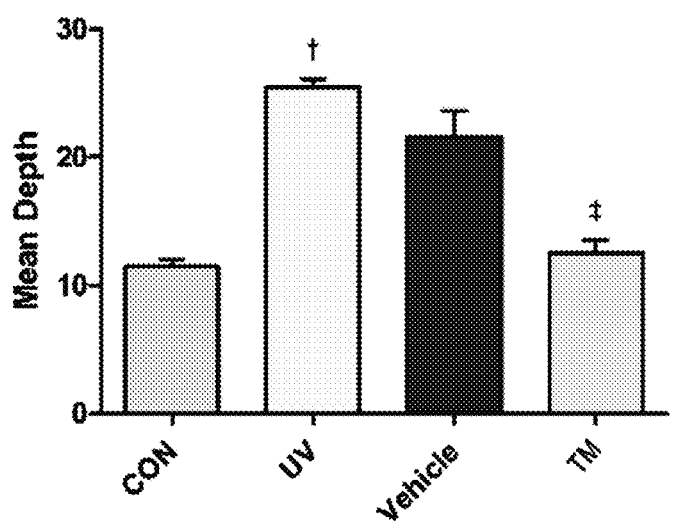
FIG. 3 shows a graph illustrating the changes in the mean depth of a skin wrinkle of hairless mice according to one embodiment of the present invention.

Further, as shown in FIG. 3, it was confirmed that the mean wrinkle depth was increased in the UV ray treated group (UV) compared to the control group (CON) ($p<0.0001$), whereas the mean wrinkle depth was significantly reduced in the group treated by compound represented by Formula 1 (TM) compared to the UV-treated group (UV) ($p<0.0001$).

From the above results, it was confirmed that the mean wrinkle length and depth, which were increased by UV rays, were significantly reduced by treating the wrinkles with the compound represented by Formula 1 prepared in Example 1. Accordingly, it was confirmed that the compound represented by Formula 1 is effective in improving skin wrinkles, and especially, effective in alleviating the wrinkles caused by UV rays.

3) Histological Observation of Skin

To confirm the wrinkle-suppressing effect, the back skin tissues of hairless mice from each experimental group were collected, fixed in a 10% neutral formalin solution followed by washing, dehydrating, clearing, and infiltrating processes, and embedded with paraffin. After being cut into a 4 μm section, the skin tissues were stained with Hematoxylin & Eosin (H&E) and Masson's trichome. The results are shown in FIGS. 4 and 5.

Figure 4:
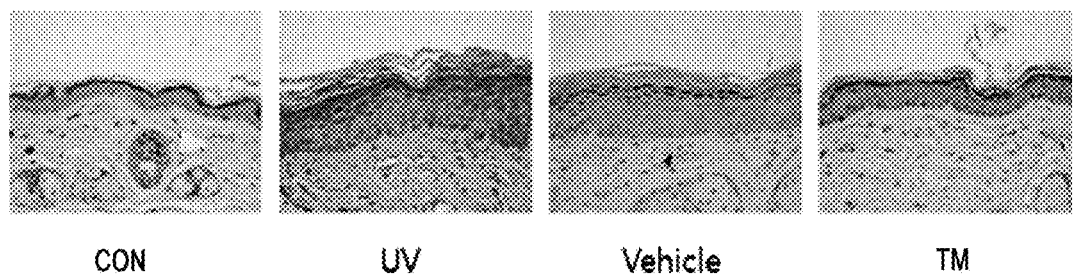
FIG. 4 is an image showing the measurement result of thickness of the cornified layers of hairless mice skin tissues via H&E staining according to one embodiment of the present invention.

As shown in FIG. 4, when the H&E staining was performed, it was confirmed that cornified layers were induced in the UV-treated group (UV) and the excipient-treated group (Vehicle) compared to the control group (CON), and thicker epidermises were also observed. Meanwhile, cornified layers were alleviated in the group treated by a compound represented by Formula 1 (TM) compared to the UV-treated group (UV) and excipient-treated group (Vehicle), and thinner epidermises were observed. Accordingly, it can be inferred that the compound represented by Formula 1 is effective in alleviating the cornified layer and reducing the epidermis thickness.

Figure 5:
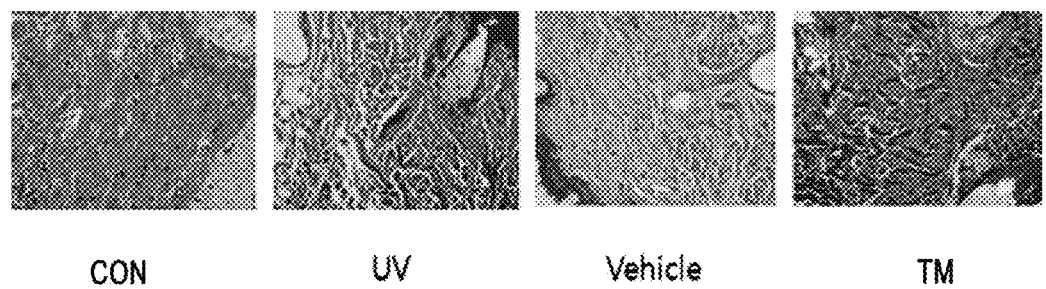
FIG. 5 is an image showing the observation result of the collagen fibers in hairless mice skin tissues via Masson's trichome staining according to one embodiment of the present invention.

Further, as shown in FIG. 5, when Masson's trichome staining was performed, it was observed that the tissues in the control group (CON), which were mostly composed of the dermis, which collagen fibers were observed throughout, whereas the collagen fibers were not observed in the UV-treated group (UV) and the excipient-treated group (Vehicle). Meanwhile, it was confirmed that collagen fibers were increased in the group treated by compound represented by Formula 1 (TM) compared to the UV-treated group (UV). Accordingly, it can be inferred that the compound represented by Formula 1 is effective in suppressing the destruction of collagen tissues caused by UV rays.

4) Analysis of Wrinkle-Suppressing Effect by Differences in Epidermis Thickness

Figure 6:
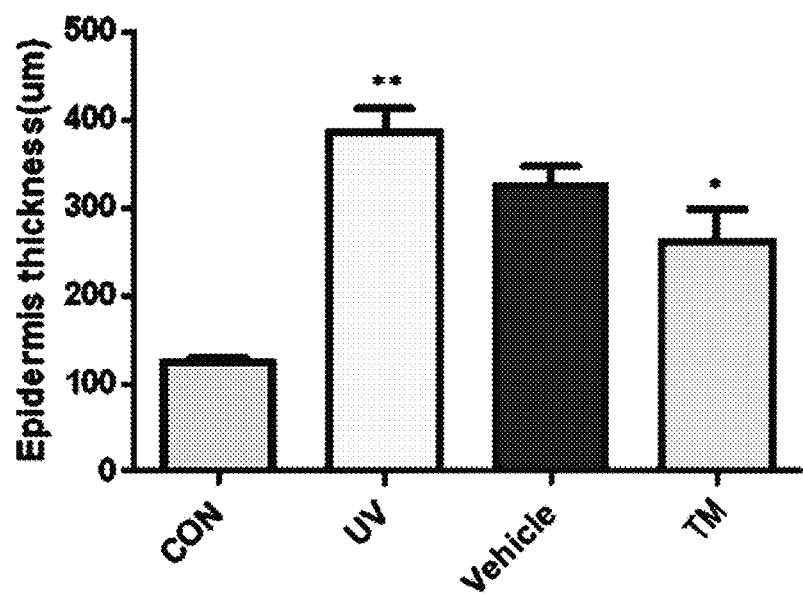
FIG. 6 is a graph showing the measurement result on epidermal thickness in H&E-stained skin tissues of hairless mice according to one embodiment of the present invention.

The epidermis thickness was measured from the keratin layer to the epidermal basement membrane of tissues, which were stained with H&E in Experimental Example 3), by a ruler installed in a microscope, and the result is shown in FIG. 6.

As shown in FIG. 6, it was confirmed that the epidermis thickness was increased in the UV-treated group (UV) due to the exposure to UV rays ($p<0.0001$). Further, the epidermis thickness was significantly reduced in the group treated by compound represented by Formula 1 (TM) ($p<0.05$).

5) Transepidermal Water Loss (TEWL) Analysis

To confirm the skin-moisturizing effect, the transepidermal water loss analysis was carried out with back skins of hairless mice in each experimental group. The transepidermal water loss level refers to the water quantity diffused from a skin, and if the level is high, it would mean that the skin moisturizing function is weakened, and that the function of innate skin barrier is damaged. To measure the transepidermal water loss, the quantity ($g/m^2/hr$) of water evaporated from the skins was calculated according to the area and time using Tewameter (Tewameter Courage & Khazaka, Germany) under constant temperature and humidity (at 23° C., relative humidity: 50%). The evaporated water quantity was then measured using Tewameter, and the skin moisturizing-ability was calculated. The result is shown in FIG. 7.

Figure 7:
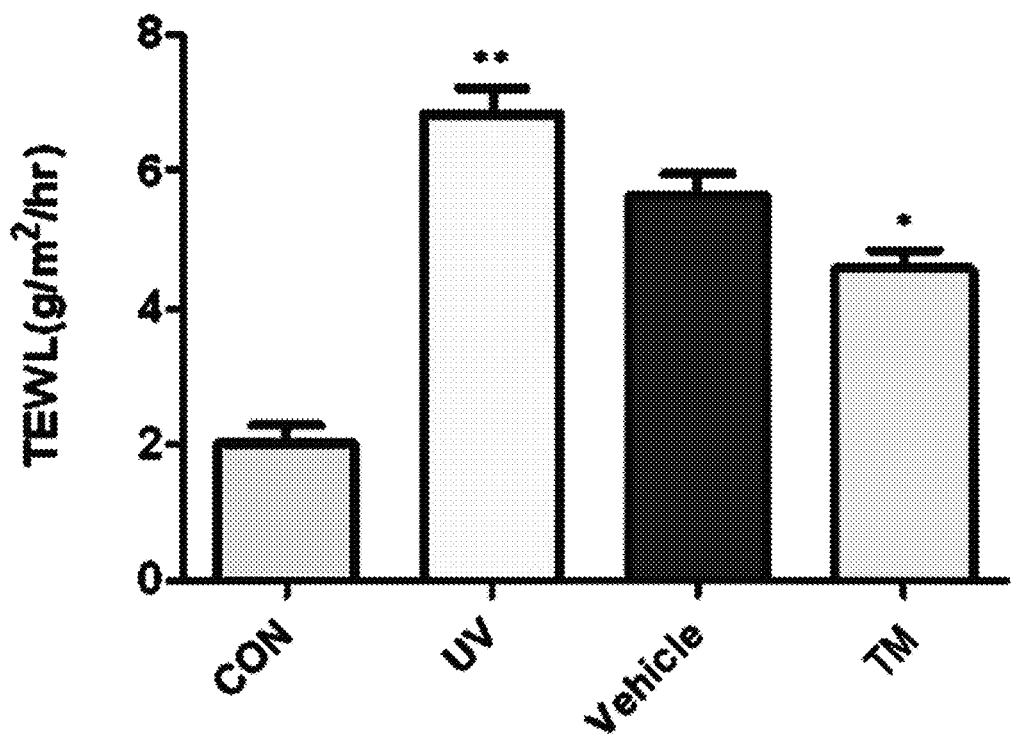
FIG. 7 is a graph showing the measurement result of transepidermal water loss of hairless mice according to one embodiment of the present invention.

As shown in FIG. 7, it was confirmed that the skin moisturizing-ability was reduced due to damage in the skin bather resulted from UV irradiation ($p<0.0001$), and that the skin water loss induced by UV rays was significantly prevented ($p<0.01$) when the skins were treated with the compound represented by Formula 1. Accordingly, the compound represented by Formula 1 is effective in moisturizing skin.

In all experimental results, significance between the control group and the experimental groups was determined using a one-way ANOVA and a Student t-test ($p<0.05$).

Hereinafter, Formulation Examples of the cosmetic composition including the compound represented by Formula 1 will be described. However, these examples are shown for illustrative purposes only and are not intended to limit formulation of the cosmetic composition of the present invention.

FORMULATION EXAMPLE 1:

Preparation of Softening Cosmetic Water (Toner)

Among the cosmetics containing the compound represented by Formula 1 of the present invention, a Formulation Example of softening cosmetic water (toner) is shown in Table 2 below.

TABLE 2

| NO. | Raw Materials | Unit (weight %) |
| --- | --- | --- |
| 1 | Compound represented by Formula 1 | 0.1 |
| 2 | Glycerin | 3.0 |
| 3 | Butylene glycol | 2.0 |
| 4 | Propylene glycol | 2.0 |
| 5 | Polyoxyethylene (60) hydrogenated castor oil | 1.00 |
| 6 | Ethanol | 10.0 |
| 7 | Triethanolamine | 0.1 |
| 8 | Preservative | Small amount |
| 9 | Coloring | Small amount |
| 10 | Flavoring | Small amount |
| 11 | Purified water | Residual amount |
| | Total | 100 |

Among the raw materials of Table 2, NOS: 2, 3, 4 and 8 were added to NO: 11 in sequence, and the resultant was stirred and dissolved. And then, NO: 5 was dissolved by being heated at around 60° C. and added with NO: 10, and the resultant was stirred and added to the above mixture of NO: 11 containing NOS: 2, 3, 4, and 8. Lastly, NOS: 1, 6, 7, and 9 were added to the mixture of NO: 11, stirred sufficiently, and passed through a microfluidizer to age the mixture.

FORMULATION EXAMPLE 2:

Preparation of Nutritive Cosmetic Water (Milky Lotion)

Among the cosmetics containing the compound represented by Formula 1 of the present invention, a Formulation Example of nutritive cosmetic water (milky lotion) is shown in Table 3 below.

TABLE 3

| NO. | Raw Materials | Unit (weight %) |
| --- | --- | --- |
| 1 | Compound represented by Formula 1 | 0.1 |
| 2 | Sitosterol | 1.70 |
| 3 | Polyglyceryl-2 oleate | 1.50 |
| 4 | Ceteareth-4 | 1.2 |
| 5 | Cholesterol | 1.5 |
| 6 | DEA-Cetyl Phosphate | 0.4 |
| 7 | Concentrated Glycerin | 5.0 |
| 8 | Sunflower oil | 10.0 |
| 9 | Carboxy vinyl polymer | 0.2 |
| 10 | Xanthan Gum | 0.3 |
| 11 | Preservative | Small amount |
| 12 | Flavoring | Small amount |
| 13 | Purified water | Residual amount |
| | Total | 100 |

Among the raw materials of Table 3, NOS: 2, 3, 4, and 5 were homogenized under a constant temperature, and the resultant was named non-ionic amphipathic lipids, which were mixed with NOS: 1, 6, 7, and 13, and the resultant was homogenized at a constant temperature, passed through a microfluidizer, and homogenized by being slowly added with NO: 8 at a constant temperature followed by being passed through a microfluidizer once again. The resultant was added with NOS: 9, 10, 11, and 12, dispersed to be stabilized, and aged.

FORMULATION EXAMPLE 3:

Preparation of Nourishing Cream

Among the cosmetics containing the compound represented by Formula 1 of the present invention, a Formulation Example of nourishing cream is shown in Table 4 below.

TABLE 4

| NO. | Raw Materials | Unit (weight %) |
| --- | --- | --- |
| 1 | Compound represented by Formula 1 | 0.1 |
| 2 | Sitosterol | 4.0 |
| 3 | Polyglyceryl-2 oleate | 3.0 |
| 4 | Ceteareth-4 | 2.0 |
| 5 | Cholesterol | 3.0 |
| 6 | DEA-Cetyl Phosphate | 0.4 |
| 7 | Concentrated Glycerin | 5.0 |
| 8 | Sunflower oil | 22.0 |
| 9 | Carboxy vinyl polymer | 0.5 |
| 10 | Triethanolamine | 0.5 |
| 11 | Preservative | Small amount |
| 12 | Flavoring | Small amount |
| 13 | Purified water | Residual amount |
| | Total | 100 |

Among the raw materials of Table 4, NOS: 2, 3, 4, and 5 were homogenized under a constant temperature, and the resultant was named non-ionic amphipathic lipids, which were mixed with NOS: 1, 6, 7, and 13, and the resultant was homogenized at a constant temperature, passed through microfluidizer, and homogenized by being slowly added with NO: 8 at a constant temperature followed by being passed through a microfluidizer once again. The resultant was added with NOS: 9, 10, 11 and 12, dispersed to be stabilized, and aged.

INDUSTRIAL APPLICABILITY

The composition containing the compound represented by Formula 1 extracted from *Anemarrhena asphodeloides* Bunge according to the present invention or the pharmaceutically acceptable salt thereof is effective in moisturizing skin and improving wrinkles, especially, preventing or alleviating wrinkles by preventing the skin moisture loss and suppressing the skin tissue damages induced by UV rays.

Accordingly, the composition may be usefully applied to an external skin application or cosmetics having skin-moisturizing and wrinkle-improving effects.

The invention claimed is:

1. A method for preventing transdermal water loss or suppressing skin wrinkles comprising applying a composition to skin of a subject having UV-induced skin aging, wherein the composition comprises a chromatographically purified compound from *Anemarrhena asphodeloides* Bunge represented by Formula 1, or a pharmaceutically acceptable salt thereof as an active ingredient:

[Formula 1]
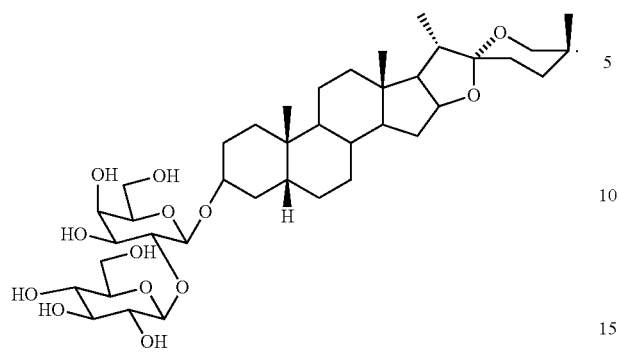
* * * * *